(12) United States Patent  (10) Patent No.: US 8,828,040 B2
Goff  (45) Date of Patent: Sep. 9, 2014

(54) DEVICE AND METHODS FOR DELIVERY AND TRANSFER OF TEMPORARY RADIOPAQUE ELEMENT

(76) Inventor: Thomas G. Goff, Mountain View, CA (US)

( * ) Notice: Subject to any disclaimer, the term of this patent is extended or adjusted under 35 U.S.C. 154(b) by 328 days.

(21) Appl. No.: 12/831,048

(22) Filed: Jul. 6, 2010

(65) Prior Publication Data

US 2011/0009818 A1 Jan. 13, 2011

Related U.S. Application Data

(60) Provisional application No. 61/223,640, filed on Jul. 7, 2009.

(51) Int. Cl.
*A61M 29/00* (2006.01)
*A61M 5/32* (2006.01)
*A61M 31/00* (2006.01)
*A61F 2/24* (2006.01)
*A61B 8/14* (2006.01)

(52) U.S. Cl.
USPC ..... 606/194; 604/265; 604/103.02; 623/2.11; 600/467; 600/470

(58) Field of Classification Search
USPC ............... 606/1, 191–192; 600/467; 604/265, 604/103.1, 103.02; 623/2.11
See application file for complete search history.

(56) References Cited

U.S. PATENT DOCUMENTS

| 5,102,402 | A | * | 4/1992 | Dror et al. ..................... 604/265 |
| 5,728,065 | A | * | 3/1998 | Follmer et al. ............. 604/96.01 |
| 5,868,719 | A | * | 2/1999 | Tsukernik ..................... 604/265 |
| 5,893,840 | A | * | 4/1999 | Hull et al. ................ 604/103.02 |
| 6,364,856 | B1 | * | 4/2002 | Ding et al. ............... 604/103.02 |
| 7,081,096 | B2 | * | 7/2006 | Brister et al. .................. 600/549 |
| 7,147,663 | B1 | * | 12/2006 | Berg et al. ..................... 623/2.38 |
| 2002/0082683 | A1 | | 6/2002 | Stinson et al. |
| 2002/0095205 | A1 | | 7/2002 | Edwin et al. |
| 2002/0111590 | A1 | * | 8/2002 | Davila et al. .................. 604/265 |
| 2003/0036792 | A1 | | 2/2003 | Richter et al. |
| 2003/0060872 | A1 | | 3/2003 | Gomringer et al. |
| 2005/0075662 | A1 | * | 4/2005 | Pedersen et al. .............. 606/194 |
| 2006/0122683 | A1 | * | 6/2006 | Stinson .......................... 623/1.1 |

(Continued)

FOREIGN PATENT DOCUMENTS

| CN | 1929891 A | 3/2007 |
| CN | 2905092 Y | 5/2007 |
| WO | WO 2006/114783 A2 | 11/2006 |
| WO | WO 2006/114783 A3 | 6/2007 |

OTHER PUBLICATIONS

International Search Report and Written Opinion of PCT Application No. PCT/US2010/041237, mailed Aug. 31, 2010, 8 pages total.

(Continued)

*Primary Examiner* — Darwin Erezo
*Assistant Examiner* — Richard Louis
(74) *Attorney, Agent, or Firm* — Wilson Sonsini Goodrich & Rosati

(57) ABSTRACT

A device for the transfer of radiopaque material within the body comprises a valvuloplasty or other balloon coated with the radiopaque material. The balloon is inflated in the aortic valve for marking the site of an aortic annulus to enable accurate placement of prosthetic valves under fluoroscopic imaging.

15 Claims, 4 Drawing Sheets

(56) References Cited

U.S. PATENT DOCUMENTS

| | | |
|---|---|---|
| 2006/0280858 A1 | 12/2006 | Kokick |
| 2007/0073391 A1* | 3/2007 | Bourang et al. ............. 623/2.11 |
| 2008/0009746 A1* | 1/2008 | Forster et al. ................. 600/467 |
| 2009/0187144 A1* | 7/2009 | Jayaraman ............... 604/103.02 |
| 2009/0254063 A1* | 10/2009 | Oepen et al. .................. 604/509 |
| 2010/0076548 A1* | 3/2010 | Konno .......................... 623/2.1 |

OTHER PUBLICATIONS

European search report dated Oct. 25, 2012 for EP Application No. 10797796.9.

\* cited by examiner

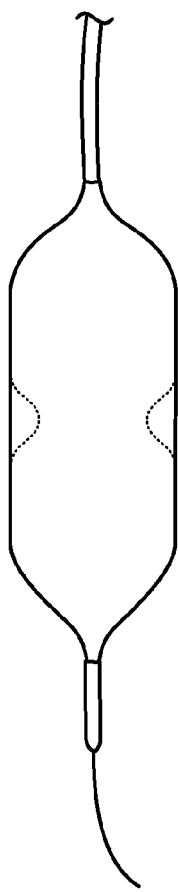
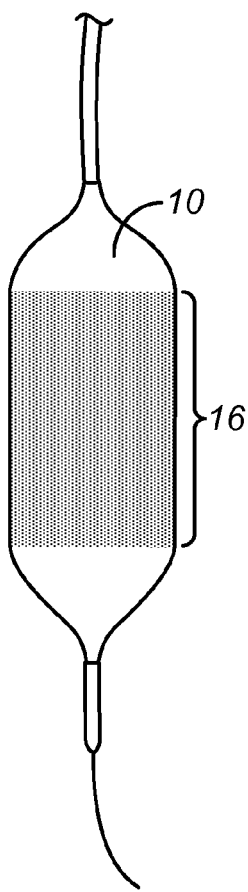
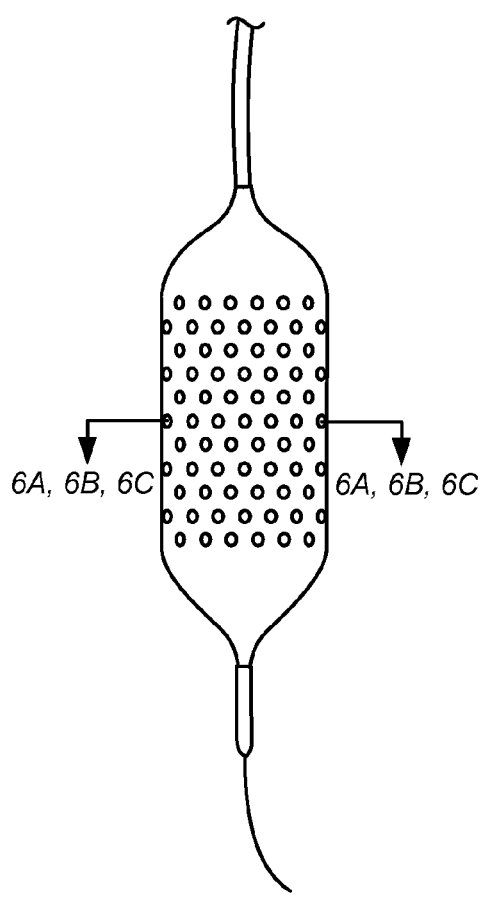
FIG. 4
*(PRIOR ART)*
FIG. 5
FIG. 6
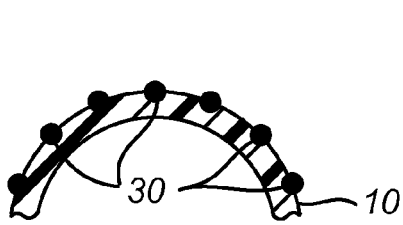
FIG. 6A
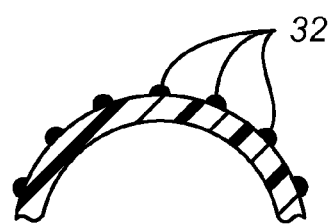
FIG. 6B
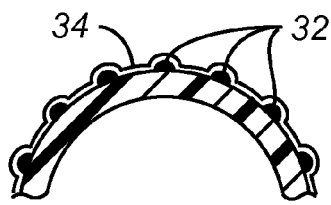
FIG. 6C

DEVICE AND METHODS FOR DELIVERY AND TRANSFER OF TEMPORARY RADIOPAQUE ELEMENT

CROSS-REFERENCES TO RELATED APPLICATIONS

The present application claims the benefit of U.S. Provisional Patent Application No. 61/223,640, filed Jul. 7, 2009, the entire contents of which are incorporated herein by reference.

BACKGROUND OF THE INVENTION

Many complex medical interventions rely on the imaging of internal body structures through less invasive means to identify structures and perform procedures without direct visualization. Such indirect visualization means include radiographic imaging such as x-ray fluoroscopy, echocardiography, ultrasound, nuclear magnetic resonance imaging, and tomography. As medical techniques continually evolve to be less invasive, these imaging techniques become more necessary.

X-ray fluoroscopy is used during many percutaneous and natural orifice surgical procedures and intravascular cardiovascular procedures. Percutaneous transcatheter procedures have become the standard of care for many cardiovascular conditions. These procedures rely on x-ray fluoroscopy, coupled with the injection of radiopaque dye to visualize the structures and paths of the circulatory system. Recently, advances have enabled the percutaneous transcatheter placement of valve prostheses.

Accurate placement of a valve prosthesis during transcatheter procedures is a significant challenge that carries substantial risks. During transcatheter aortic valve replacement (TAVR), operators perform Rapid Ventricular Pacing (RVP) to limit the heart motion and improve the chance of an accurate valve deployment. These procedures are done under fluoroscopy. Prior to the placement of the valve prosthesis, Balloon Aortic Valvuloplasty (BAV) is performed to open up the diseased aortic valve. It has been well documented in the early experience with these devices that failure to accurately place the valve prosthesis can result in devastating complications including embolization of the valve into the left ventricle, embolization of the valve into the aorta, and obstruction of the coronary arteries by the valve. These complications are associated with a high incidence of procedure-related death. The geometry of the aortic structures is such that there is only a limited landing zone for the valve to be effective. This limited target zone, when coupled with the movement of the beating heart, creates a difficult procedure with a high complication rate. Advanced vascular disease further complicates the placement.

SUMMARY OF THE INVENTION

The present invention provides a novel device which is useful for balloon aortic valvuloplasty (BAV) and other procedures performed under fluoroscopic imaging. The device comprises a balloon coated, impregnated, or otherwise carrying a radiopaque material, component or element (referred to hereinafter as a "radiopaque material"). During the BAV, this radiopaque material is transferred to the walls and surfaces of the patient's native aortic valve and annulus, thereby making the target zone for placement of a prosthetic valve clearly visible under fluoroscopy. Such improved imaging and targeting provides many significant advantages for the accurate placement of the prosthetic aortic valve. While the methods will most often be performed using a modified valvuloplasty balloon, they could also be performed with other catheters or devices prior to valvuloplasty. By performing simultaneously with the valvuloplasty procedure, however, no additional steps are required and the benefits are gained with minimum complication of the procedure.

In a first aspect of the present invention, a method for marking a luminal site, such as an aortic valve site including at least one of an aortic root, aortic valve, and aortic valve annulus, comprises providing an expandable member having a radiopaque material releasably carried on an external surface thereof. As noted above, the expandable member will usually be an inflatable valvuloplasty balloon on a valvuloplasty catheter, but could also comprise other mechanically expandable cages, scaffolds, coils, braids, or the like, which have dimensions sufficient to be expanded within the aortic valve site to provide the desired marking. The expandable member is expanded within the luminal site to transfer at least a portion of the radiopaque material to the luminal site so that visibility of said portion is enhanced under fluoroscopic or other X-ray-based imaging techniques. In the case of transvascular aortic valve replacement (TAVR), the marking of the aortic valve site allows placement of the prosthetic valve with much greater accuracy than has been previously achieved.

While the expansion of the expandable member within the luminal site can be performed separately from valvuloplasty or any other interventional protocol, it will usually be performed simultaneously with an initial valvuloplasty procedure carried out prior to native valve ablation and/or prosthetic valve implantation. As is well known in the art, valvuloplasty relies on inflation of a balloon within the valve leaflets in order to break calcification present on or between the leaflets so that the leaflets are immobilized. Usually, the valvuloplasty balloon is inflated to a pressure in the range from 0.1 atmospheres to 20 atmospheres, typically from 3 atmospheres to 5 atmospheres, and the radiopaque materials carried on the expandable member will be coated, attached, sequestered, or otherwise releasably coupled to the external surface of the expandable member so that they will release and transfer to the luminal wall upon inflation within these pressure ranges.

The radiopaque material may be sequestered or otherwise immobilized on the external surface of the expandable member in a variety of ways. For example, the radiopaque material may be a conventional radiopaque dye, as described hereinbelow, which may be coated over a portion of the surface of the balloon, either with or without a suitable carrier compound. In other instances, the radiopaque material may be folded within the lobes or other layers of the balloon as the collapsed balloon on the delivery catheter so that the material is released on balloon inflation. In still other instances, the radiopaque material may be disposed in a porous structure of the expandable member, either being in the wall of the expandable member itself or in a porous coating placed over the wall. In still other embodiments, the radiopaque material may be disposed in a plurality of wells or "dimples" formed on the external surface of the expandable member, while in still other embodiments, the radiopaque material may be present on the external surface as a plurality of microdots, frequently being in the form of microencapsulated pellets or beads which are sequestered on the surface. In still further embodiments, the radiopaque material may be secured to an external surface of the expandable member beneath a porous or frangible (breakable) membrane which will release the material upon inflation of the balloon to a predetermined pressure and/or diameter. A variety of other techniques for sequestering material may also be employed.

In a second aspect of the present invention, a catheter for marking a luminal site comprises a catheter body having a proximal end and a distal end and an expandable member on the distal end. The radiopaque material is releasably carried on an external surface of the expandable member, and the material is coupled to the surface such that at least a portion of the material will transfer to a luminal surface when the member is expanded therein. Typically, the expandable member will be an inflatable balloon, more typically a balloon of the type used for valvuloplasty, usually being non-distensible, having an uninflated diameter in the range from 3 Fr (1 French=0.33 mm) to 20 Fr, usually in the range from 9 Fr to 14 Fr, an inflated diameter in the range from 10 mm to 60 mm, usually in the range from 22 mm to 30 mm, a length in the range from 15 mm to 80 mm, usually in the range from 40 mm to 60 mm, and inflatable to a pressure in the range from 0.1 atmospheres to 20 atmospheres, usually from 3 atmospheres to 10 atmospheres.

The radiopaque dye or other material is coated over at least a portion of the surface of the expandable member generally using any of the techniques and protocols described above or hereinafter.

BRIEF DESCRIPTION OF THE DRAWINGS

FIG. 4 illustrates a prior art valvuloplasty balloon having no radiopaque material thereon.

FIG. 5 illustrates a modified valvuloplasty balloon having a radiopaque material coated over an external surface thereof.

FIGS. 6 and 6A-6C illustrate a valvuloplasty balloon having a variety of other surface modifications for sequestering a radiopaque material in accordance with the principles of the present invention, with details of particular modifications shown in FIGS. 6A-6C.

DETAILED DESCRIPTION OF THE INVENTION

Figure 1:
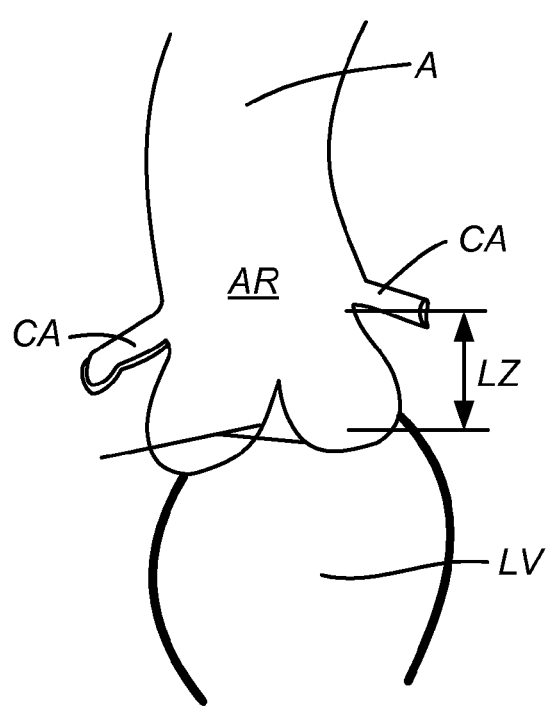
FIG. 1 illustrates the anatomy of an aortic root of a human patient.

FIG. 1 shows the geometry of the aortic root AR. Of note is the narrow landing zone LZ for a prosthetic valve. This zone is bounded by the aorta A and coronary arteries CA above and the left ventricle LV below. This narrow working space makes the percutaneous placement of a prosthetic aortic valve very challenging.

Figure 2:
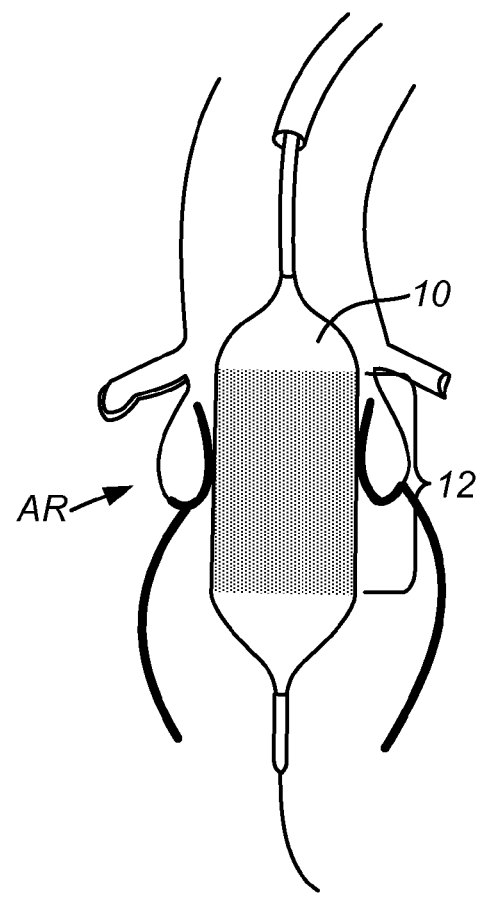
FIG. 2 illustrates a valvuloplasty balloon which has been coated with a radiopaque material in accordance with the principles of the present invention expanded within the aortic root.
Figure 3:
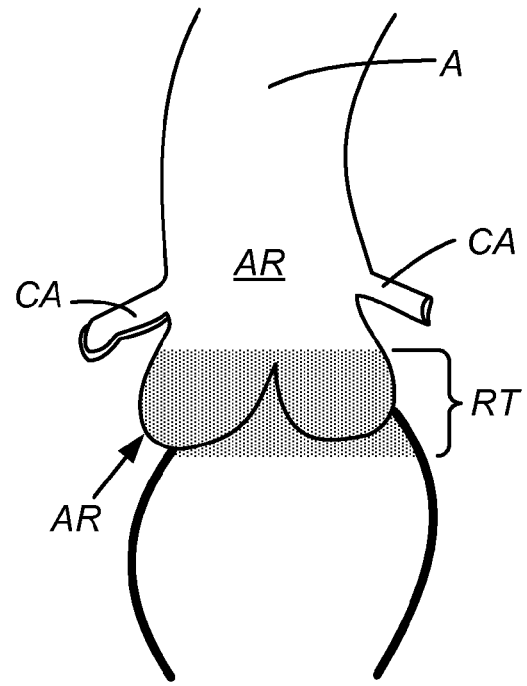
FIG. 3 illustrates the transfer of radiopaque material resulting upon the inflation of the valvuloplasty balloon as illustrated in FIG. 2.

FIG. 2 shows a balloon 10 coated with a radiopaque dye 12 or other radiopaque material during a balloon aortic valvuloplasty in the aortic root AR. During this inflation, the radiopaque material will be transferred to the surrounding tissues, where FIG. 3 shows the region of transfer RT of the radiopaque material. Since the prosthetic valve is desired to be placed at the annulus, or region of greatest narrowing, the radiopaque element will naturally have transferred to the desired transfer region as the expanding balloon will engage the narrowest region first.

FIG. 4 shows a standard valvuloplasty balloon. Such valvuloplasty balloons are available from a number of manufacturers, such as Toray Medical Co., Ltd., Tokyo, Japan; Cordis Corporation, Miami Lakes, Fla.; Medi-tech Division, Boston Scientific, Natick, Mass.; Edwards Life Sciences, Irvine, Calif., and will have the dimensions and characteristics described above. Although FIG. 4 shows a straight cylindrical balloon, in practice many valvuloplasty balloons have a slight waist, or region of narrower diameter in the center, to accommodate the valve geometry, as shown in broken line in FIG. 4 Such a balloon profile could be employed in any of the embodiments of the present invention and in some instances may help locate or center the balloon within the annulus and may improve transfer of the radiopaque material to the surfaces of the annulus.

The surface of the conventional balloon may be coated with or otherwise modified to carry the radiopaque material, usually within most or all of the cylindrical central region 16 of the balloon 10, as illustrated in FIG. 5. By coating the entire middle cylindrical section 16, the likelihood that the radiopaque material will actually be transferred to the region of transfer RT (FIG. 3) is greatly enhanced since the need to axially align the balloon prior to inflation is greatly reduced.

FIGS. 6 and 6A-6C show three types of potential balloon surface treatments to enhance the delivery and transfer of the radiopaque material. As shown in FIG. 6A, indented wells 30 can be formed over the central section 16 of the balloon surface to contain the radiopaque material. As shown in FIG. 6B, raised dots 32 could consist of a gel mixed with the radiopaque material. Such dots or microdots can be formed into adherent admixtures which are applied as droplets onto the balloon surface and which fix to the surface as they dry or cure. As shown in FIG. 6C, the radiopaque material can be maintained on the external surface of the balloon using a membrane 34. The radiopaque material may comprise microdots 32 or other layers or sources of the radiopaque material.

Figure 7A:
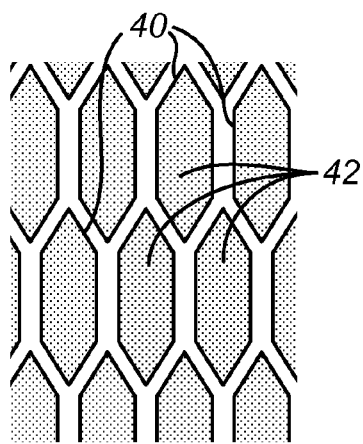
FIGS. 7A and 7B illustrate a balloon modification where the balloon comprises sponge-like pores which carry radiopaque dye in the unexpanded configuration (FIG. 7A) and releases the dye in the expanded configuration (FIG. 7B).
Figure 7B:
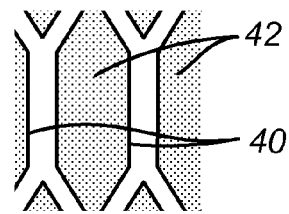

Referring now to FIGS. 7A and 7B, the external balloon surface, or another layer of material applied over the balloon surface, can be formed with sponge-like pores 40 which hold the radiopaque material 42. When the balloon is unexpanded, as shown in FIG. 7A, the radiopaque material 42 is held tightly within the pores. When the balloon is expanded, as shown in FIG. 7B, however, the pores stretch and expose the radiopaque material facilitating its release.

Figure 8A:
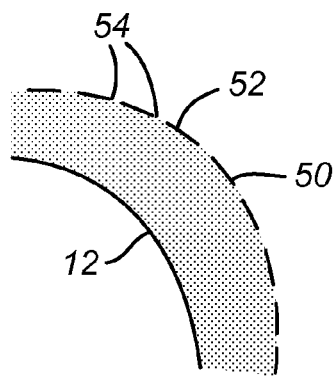
FIG. 8A illustrates a cross-section of a balloon structure carrying the radiopaque material beneath an outer, perforated surface. Balloon expansion causes release of the material, as illustrated in FIG. 8B.
Figure 8B:
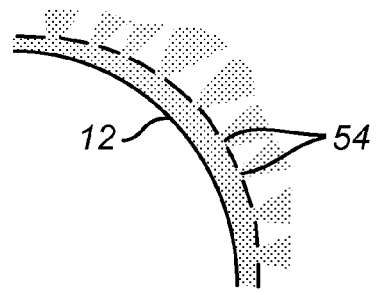

As shown in FIGS. 8A and 8B, the radiopaque material 50 may be layered over the balloon 12 with an outer, perforated layer 52 holding the radiopaque material in place, as shown in FIG. 8A. Upon balloon expansion, as shown in FIG. 8B, the inner balloon layer 12 expands and forces the radiopaque material 50 out through the perforations 54 in the outer layer, releasing the radiopaque dye as shown in FIG. 8B.

Figure 9A:
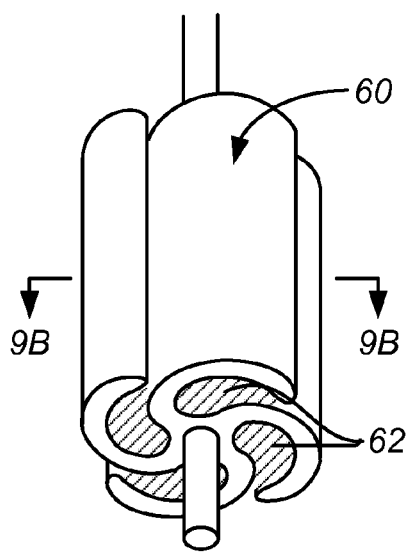
FIGS. 9A and 9B illustrate sequestration of the radiopaque material in the folds or lobes of a deflated balloon, with FIG. 9B being a cross-sectional view taken along line 9B-9B of FIG. 9A.
Figure 9B:
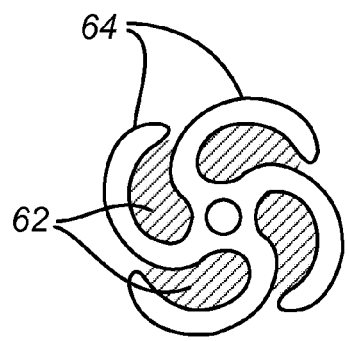

FIGS. 9A and 9B show a valvuloplasty balloon 60 folded for delivery. The balloon 60 could be folded during manufacturing. The radiopaque material 62 is sequestered between folds or "lobes" 64 of the balloon 60. This configuration allows the radiopaque material 62 to be delivered to the target site without being lost through contact with other surfaces. The material 62 is then released upon balloon inflation.

Figure 10:
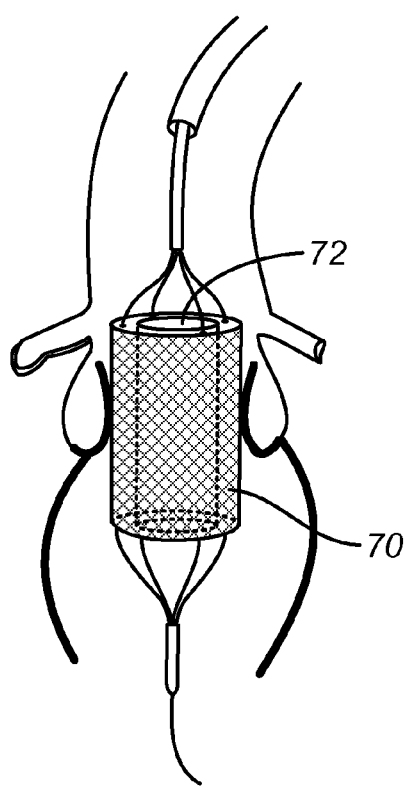
FIGS. 10-12 illustrate alternative expandable member configurations other than the modified valvuloplasty balloons described previously.

FIG. 10 shows an embodiment of the expandable member 70 that includes an inner lumen 72 to allow for flow of blood through the device while it is expanded. The radiopaque material 74 is coated over the external surface of the member 70.

Figure 11:
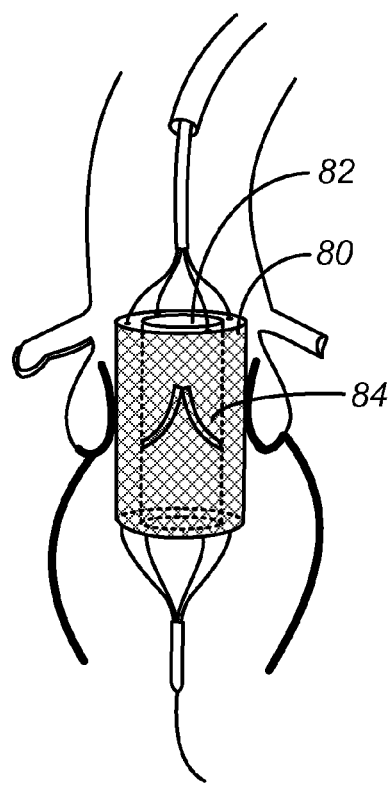

FIG. 11 shows an embodiment of the expandable member 80 that includes an inner lumen 82 to allow for flow of blood through the device while it is expanded, with the addition of an inner one-way valve 84 to assist the proper blood flow during the cardiac cycle. The radiopaque material may be provided in any of the ways described previously.

Figure 12:
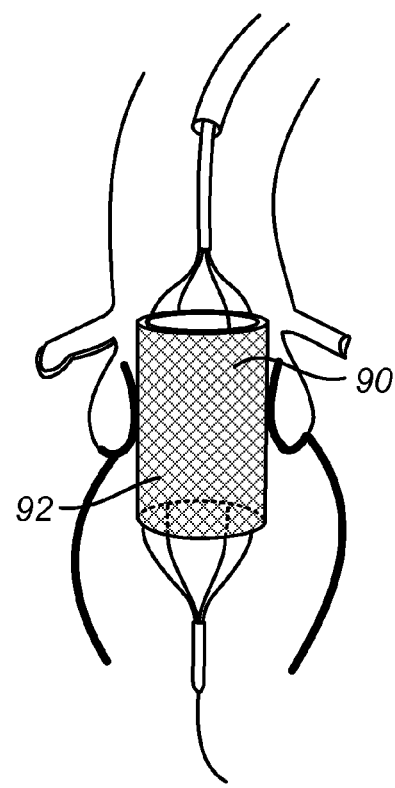

FIG. 12 shows a self-expandable annular ring member 90 which is not actuated by inflation means. The external surface 92 can be coated with radiopaque material in any of the ways described previously.

The radiopaque material may comprise a conventional medical contrast dye, as well as other radiopaque materials, such as gels, powders, dust, particles, nano-particles, liquids, stains, adhesives and the like. The material could be anywhere from 5-95% radiopaque, but preferably in the range of 70-90% radiopacity. The radiopaque material could be coated or otherwise applied in one layer or multiple layers. Such multiple layers could have different densities of the radiopaque material, such that a more complete contact with a surface inside the body would result in a darker, more radiopaque mark under fluoroscopy. This gradient of radiopaque marking would give the operator additional information about the anatomical areas of greatest restriction and resistance to expansion. The radiopaque material could be one of many currently in use in medicine, including but in no way limited to: iodine, iopromide, metallic ions, gold, barium sulfate. The radiopaque material could be mixed with a biocompatible adhesive to promote adherence to the target site. Many biocompatible radiopaque dyes and particles are currently in use in the circulatory system. The radiopaque material could be selected from one of these or part of a newly identified material with similar functional properties. The persistence of the dye or other radiopaque material would be temporary in nature, designed to last long enough to aid the procedure but not be permanent.

The balloon could be made from conventional materials such as latex, polyisoprene, rubber, polyurethane, composites, woven fiber, nylon, polyethylene, PET, combinations thereof and the like. When also used of valvuloplasty, however, the materials will usually be non-distensible. At least a portion of the surface of the balloon could be treated with folds or mini-folds designed to harbor the radiopaque element safely during delivery of the balloon to the treatment site. Alternatively, the surface of the balloon or delivery element could be treated to have a surface geometry designed to hold the radiopaque element substantially in place until deployment at the target site. This surface treatment could include wells or micro-wells filled with the radiopaque element. The surface treatment could also include fine, hair-like structures coated with radiopaque element and designed to optimize surface contact and transfer of the radiopaque element. Further, these fine, hair-like structures could be made of radiopaque material and designed to separate from the balloon and attach to the target tissue. The balloon surface could have raised micro-dots of radiopaque element in a gel form. These micro-dots of radiopaque gel could include adhesive properties to help attach to the contact surfaces within the body.

Alternatively, the balloon could be constructed from several layers of material, with the inner layers providing the desired expansion properties, and the outermost layer of the balloon could be made of an absorbent material preloaded with radiopaque element. This material could have sponge-like characteristics. The textured surface of the delivery element could contain spongy, nest-like, web-like material. It could also contain 'pores' filled with radiopaque dye. These pores, part of a loose weave, would enclose the radiopaque gel when the balloon was uninflated for delivery. Upon inflation, the fibers of this woven layer would stretch, compressing the pores and forcing the radiopaque dye out of them and onto the contact surfaces within the body. See FIGS. 7A and 7B discussed above.

One preferred embodiment would involve blisters filled with radiopaque dye. A portion of the outer surface of the balloon or delivery element would be covered with these blisters filled with radiopaque dye and covered with a pressure sensitive membrane. When the balloon or delivery element is expanded, the increase in pressure would cause the membrane to burst, releasing the radiopaque dye. The pressure membrane could be activated by the increased internal pressure of the balloon, or by the pressure between the balloon and the contact surface within the body. See FIG. 6C discussed above.

Another preferred embodiment entails radiopaque dye sandwiched between two or more layers of balloon material. The inner layer would perform as a normal valvuloplasty balloon. The outer layer would be porous or contain microperforations. These perforations cover a minority of the area, such that the radiopaque dye within the layers stays largely intact during the introduction and delivery of the catheter to the treatment site. Once the inner balloon layer is inflated, the perforations allow the radiopaque dye to pass through the outer layer and onto the contact surfaces. See FIGS. 8A and 8C discussed above.

In another embodiment, the balloon and its surface covered with the radiopaque element, could be delivered to the target site inside a protective sheath. The protective sheath would keep the radiopaque element in place during delivery. Once at the target site, the protective sheath could be pulled back to reveal the balloon with its dye coating ready for deployment. Alternatively, the protective sheath could be made of a thin material designed to fail in a predetermined fashion, triggered by the expansion of the balloon. The sheath could split in a controlled manner, revealing the radiopaque dye contained within and allowing the balloon full expansion. The split sheath would stay anchored to the balloon for withdrawal with the balloon catheter assembly.

The application of the radiopaque coating to the device could be achieved by simply submerging the balloon catheter into radiopaque dye to thoroughly coat the device just prior to introduction to the body. Likewise, the radiopaque element could be applied like paint to the surface of the balloon just prior to insertion.

In preferred embodiments, more advanced manufacturing techniques would be employed to deposit the radiopaque dye element onto the balloon or delivery element. The radiopaque element could be suspended in an aqueous solution applied to the surface during manufacturing and allowed to dry—evaporating off the water and leaving the radiopaque dye in place. Likewise, a solution based on acetone, or isopropyl alcohol could be used to speed the evaporation process. Radiopaque paint, varnish, resin, lacquer, polymer could be applied to the device. The radiopaque element could also be applied using vapor deposition or static deposition techniques. The radiopaque element could also be applied during a controlled dipping, molding, or heating process. Alternatively, the radiopaque element could be combined with an ultraviolet sensitive substrate, applied to the device, and cured into place using UV curing processes.

In another approach, sheets of radiopaque material could be fabricated in a separate process, and the sheets then attached to the balloon using adhesive, radio-frequency welding, thermal bonding or similar techniques.

In still another approach, the radiopaque material could be combined with a substance which specifically or preferentially binds to target tissue, for example, the interior surface of the aortic root.

Alternatively, radiopaque dye can be suspended in a biocompatible hydrogel, and then freeze-dried. This yields a solid which can be attached to the balloon. Upon sufficient combination with the fluids and heat of the body, the solid would liquefy, releasing the radiopaque agent onto the target surface.

Additionally, the radiopaque element could be a powder, dust, or flakes applied to the surface of the balloon.

Flow-through embodiments. The delivery element could be made to be annular in nature, such that when deployed into its expanded mode, it created a central lumen through which blood was permitted to flow. Within this central annular lumen there could be a valve to perform the basic function of the valve that is being treated. For example, in the case of transcatheter treatment of an aortic valve, the delivery element would contain an internal valve that would allow for blood flow while the element was expanded and marking the native anatomy. This could alleviate the need for Rapid Ventricular Pacing since the heart could continue with its normal contraction rhythm. This could improve patient comfort, reduce complexity of the procedure, and enable longer treatment/transfer times. Structures which could perform such duty include annular balloons and expandable ring structures built from thin scaffolding similar to stents. Such ring structures could expand when a shape memory material or similar is released from an overtube. Alternatively, the ring structures could expand when an inner slidable member is pulled proximally to shorten the distance between the distal and proximal anchoring points of the structure.

Marking the aortic annulus with a radiopaque element provides for the safe, accurate placement of the valve prosthesis. This reduces the amount of guesswork by the operator for where to place the valve. Better visibility of the native valve structures provides increased ease-of-use for the valve implantation procedure. Easier procedures have an associated shortened learning curve for new operators. As these new percutaneous valve procedures move out of the hands of the expert operators and into general use, such ease-of-use advantages have an amplified impact on outcomes. This invention should help reduce the number of procedure-related complications due to misplacement of the valve prosthesis. Additionally, with the structures of the aortic valve better visualized due to the dye, the amount of contrast dye injections during procedure for visualization should be reduced. This reduces the harmful burden of the radiopaque dye on the kidneys and other organs. Significantly, with the improved visualization provided by this invention, the need for additional visualization through Trans Esophageal Echocardiography (TEE) and TransThoracic Echocardiography (TTE) should be greatly reduced. This provides a significant cost savings including devices and professional services from an echocardiographer.

While a preferred embodiment is described herein, there are several more complex means of achieving similar results that can be contemplated by one skilled in the art. Among these are the following. The addition of a lumen to the BAV device through which to deliver the radiopaque element, for example to a perforated weeping outer surface of the balloon. Another more complex means would entail providing for a system in which the radiopaque elements are deployed selectively by the operator through activation of an electrical control for deployment. Of course, a small radiopaque implant could be delivered as well, such as a staple or other simple marker visible under fluoroscopy. However, this has the additional disadvantage of a permanent implant. To overcome this disadvantage, the small radiopaque implants could be made from bioabsorbable materials and designed to fully absorb without trace within a set period of time.

A further embodiment could involve the deployment of an echogenic material. Often during transcatheter interventions echocardiography is used to provide additional visualization of the heart structure and vasculature. Instead of or in addition to the radiopaque dye, the device could deliver a dye that would appear on echocardiography. One such material would be microbubbles. Alternatively, the device could deploy an agent substance onto the internal target structures which attracted systemically-introduced microbubbles.

The catheters of the present invention may be useful in the treatment of other internal structures, a different geometry device may be preferred for delivering the radiopaque element. For instance, in the treatment of mitral valve disease and disorders, the chordae of the valve often create a challenge for the delivery of treatment devices. Sometimes devices become tangled in the chordae and can damage them. For these reasons, it could be advantageous to mark the chordae with a radiopaque element to make them more visible to the operator. In addition to the balloon described elsewhere here, a device with a deflectable, steerable swab or brush element could selectively apply the radiopaque element. This element could have the form of a soft, spherical tip and be impregnated with radiopaque element. It could also have a lumen through which the radiopaque element could be delivered to its tip. Alternatively, the tip of the element could have the form of an expandable ring to mark structures in all directions.

The enhanced visualization of the valve chordae would improve the ease of treatment and help prevent damage to the structures.

The marking catheter of the present invention could be used to internally mark other luminal surfaces for better visualization during many procedures including gastrointestinal, general surgery, ENT surgery, orthopedics, and endoscopic procedures.

What is claimed is:

1. A method for marking a valve structure in a heart, said method comprising:
   providing an expandable member having a radiopaque material releasably carried on an external surface thereof;
   expanding the expandable member within the valve structure in the heart to transfer at least a portion of the radiopaque material to an implantation site in the valve structure prior to implanting a prosthetic valve at the implantation site;
   removing the expandable member from the valve structure after the radiopaque material has been transferred to the implantation site; and
   fluoroscopically imaging the transferred radiopaque material on the valve structure, wherein the radiopaque material delineates the implantation site on the valve structure prior to implantation of the prosthetic valve.

2. A method as in claim 1, wherein the valve structure comprises an aortic valve site and the implantation site includes at least one of an aortic root, aortic valve, and aortic valve annulus.

3. A method as in claim 2, further comprising:
implanting the prosthetic aortic valve at the implantation site.

4. A method as in claim 3, wherein expanding the expandable member comprises inflating a balloon within the aortic valve site.

5. A method as in claim 4, wherein said balloon inflation opens the valve leaflets and breaks calcification present on or between the leaflets.

6. A method as in claim 5, wherein the balloon is inflated to a pressure in the range from 0.1 atmosphere to 20 atmospheres.

7. A method as in claim 1, wherein the radiopaque material is coated over at least a portion of the surface of the expandable member.

8. A method as in claim 1, wherein the radiopaque material is disposed in a porous structure of the expandable member.

9. A method as in claim 1, wherein the radiopaque material is disposed in wells found on the external surface of the expandable member.

10. A method as in claim 1, wherein the radiopaque material is present on the external surface as a plurality of microdots.

11. A method as in claim 1, wherein the radiopaque material is present on the external surface under a membrane.

12. A method as in claim 1, wherein the valve structure comprises mitral valve chordae.

13. A method as in claim 1, further comprising removing expandable member prior to fluoroscopically imaging the valve structure.

14. A method as in claim 13, further comprising performing an intervention at the target site while fluoroscopically imaging the valve structure after the expandable member has been removed.

15. A method as in claim 14, wherein performing an intervention comprises placing a prosthetic valve at the target site.

* * * * *